Figure 1:
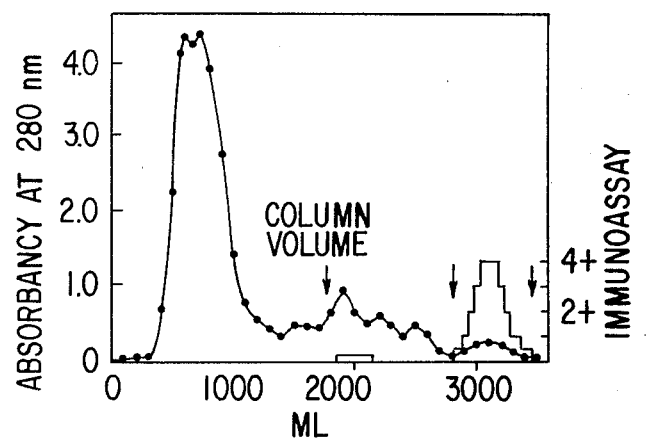

United States Patent [19]

Cohen et al.

[11] 3,948,875

[45] Apr. 6, 1976

[54] PROCESS FOR THE PREPARATION OF EPIDERMAL GROWTH FACTOR AND NEW DERIVATIVE USING CROSS-LINKED POLYACRYLAMIDE GEL AT pH OF 1-3

[76] Inventors: Stanley Cohen, 3708 Wimbledon Road, Nashville, Tenn. 37215; C. Richard Savage, Jr., 921 Pine Hill Drive, West, Schenectady, N.Y. 12303

[22] Filed: Nov. 27, 1973

[21] Appl. No.: 419,231

[52] U.S. Cl. .................. 260/112 R; 424/85; 424/95
[51] Int. Cl.² ............................................ C07G 7/00
[58] Field of Search .................... 260/112 R; 424/95

[56] References Cited
OTHER PUBLICATIONS

Chem. Abstracts, Vol. 61, 1964, 8695d, Cohen.
J. of Biol. Chemistry, Vol. 247, Dec. 1972, Savage et al., pp. 7612–7621.
J. of Biol. Chem., Vol. 237, 1962, pp. 1555–1562, Cohen.
J. of Biol. Chem., Vol. 247, Dec. 1972, Savage et al., pp. 7609–7611.
Chem. Abstracts, Vol. 62, 1965, 9381b–9381c, Salvi et al.
J. of Biol. Chemistry, Vol. 247, Sept. 25, 1972, Taylor et al.

*Primary Examiner*—Howard E. Schain
*Attorney, Agent, or Firm*—Larson, Taylor and Hinds

[57] ABSTRACT

A new procedure has been devised for the preparation of pure epidermal growth factor (EGF) in high yield which involves passing homogenates of submaxillary glands of adult male mice through a polyacrylamide gel cclumn of a low acid pH. Preferably a two step procedure is used wherein the fraction obtained from the polyacrylamide gel chromatography is subjected to DEAE-cellulose chromatography.

The new procedure also provides a new derivative of EGF, lacking the COOH-terminal Leu-Arg residues.

15 Claims, 2 Drawing Figures

PROCESS FOR THE PREPARATION OF EPIDERMAL GROWTH FACTOR AND NEW DERIVATIVE USING CROSS-LINKED POLYACRYLAMIDE GEL AT A PH OF 1-3

The invention described herein was made in the course of work under a grant or award from the Department of Health, Education and Welfare.

BACKGROUND OF THE INVENTION

1. Field of the Invention

This invention relates to a process for the production of pure epidermal growth factors in high yield from crude extracts of the submaxillary glands of adult male mice.

2. Description of the Prior Art

In 1962, Stanley Cohen in the *Journal of Biological Chemistry*, Vol. 237, page 1555, reported the isolation from the submaxillary glands of adult male mice of a polypeptide which stimulates the proliferation of various epidermal and epithelial tissues both in vivo and in vitro. The isolated polypeptide has been termed epidermal growth factor and studies on its biological properties, biosynthesis and mechanism of action have been reviewed in Cohen, S. and Taylor, J. M., "Epidermal Growth Factor; Chemical and Biological Characteristics", *Epidermal Wound Healing*, edited by Maibach and Rovee, 1972 Yearbook Medical Publication, page 203.

More recently, tests with rabbits have demonstrated that topical application of the epidermal growth factor to cornea whose epithlium has been scraped off accelerates its regrowth. *Experimental Eye Research*, Vol. 15, pages 361–366 (1973).

Methods for the isolation of epidermal growth factor have been discussed in the 1962 Cohen article, supra and also in Taylor, J. M., Cohen, S., and Mitchell, W. M. (1970) *Proc. National Academy of Science, U.S.A.* Vol. 67, page 164 and Taylor, J. M., Mitchell, W. M. and Cohen, S. (1972), *Journal of Biological Chemistry*, Vol. 247, pages 5928–5934. The yields produced by these methods, however, are low and in addition the methods involve multistep procedures which are cumbersome and time-consuming.

It is an object of this invention to provide a process for increasing the yields of epidermal growth factor isolatable from the submaxillary glands of adult male mice.

It is also an object of the invention to achieve such improved yields while at the same time greatly simplifying the isolation by considerably reducing the multistep procedures heretofore required for the isolation of such epidermal growth factor.

Yet another object of the invention is to provide a derivative of the epidermal growth factor which is indistinguishable in biological activity from epidermal growth factor.

BRIEF SUMMARY OF THE INVENTION

These and other objects of the invention are obtained by homogenizing submaxillary glands of adult male mice, separating the resulting homogenate into a solid fraction and a supernatant fraction, passing the supernatant fraction through a column of crosslinked polyacrylamide gel at a pH of 1 to 3 to selectively adsorb epidermal growth factor from said supernatant fraction, eluting the column to recover a fractional eluate having epidermal growth activity and absorption of ultraviolet light of wave length about 280 $\mu$.

In a preferred embodiment of the present invention epidermal growth factors of even greater purity and improved homogeniety are obtained by adding a second purification step to the process which step comprises passing the fractional eluate having epidermal growth activity obtained from the polyacrylamide gel adsorption step through a column of diethylaminoethyl-cellulose at a pH of above about 4 to adsorb the epidermal growth factors therefrom and eluting same from the column with an increasing salt gradient.

GENERAL DESCRIPTION OF THE INVENTION

The process of the invention provides both epidermal growth factor (hereinafter referred to as EGF) and a derivative of EGF (hereinafter referred to as EGF-2) which is essentially EGF lacking the COOH-terminal Leu-Arg residues. Whether the process provides EGF or EGF-2 depends upon the final pH of the homogenate. It has been found that the crude homogenate of adult male mice submaxillary glands contains a very potent enzyme(s) which rapidly removes COOH-terminal LeuArg residues at a pH of between 3 and 4. Thus, if EGF-2 is the desired biologically active fraction the pH of the homogenate should be maintained at a pH of between 3 and 4, preferably about 3.5 to allow the enzymatic action to take place. Also, to isolate EGF-2 the two-step fractionation embodiment of the invention should be employed. On the other hand, should EGF be the desired biologically active fraction, the pH of the crude homogenate should be maintained either below 3, say down to pH 1 or above 4, say up to pH 7 so as to avoid the pH range at which the destructive enzymatic action takes place.

Should it not make any difference whether EGF or EGF-2 is obtained then obviously no attention need be paid to the pH of the crude homogenate. For purposes of this specification and the appended claims, therefore, the term "epidermal growth factors" is used as a generic expression for EGF and EGF-2.

An important feature of the present invention resides in the discovery that polyacrylamide gel selectively adsorbs at a pH of 1 to 3, preferably about 1.5, EGF and EGF-2 contained in crude homogenates of adult male mice submaxillary glands. The reason for the selectivity exhibited by crosslinked polyacrylamide gel for EGF and EGF-2 is not fully understood but it appears the ability of the gel to effect this separation is based on something more than a mere difference in molecular sizes since the biologically active material is not eluted from the column until after over 1.6 column volumes. It seems, therefore, that the polyacrylamide gel possesses at the low pH employed in the process some form of selective retentive activity with respective to the EGF and EGF-2 fractions. Accordingly, the exclusion limits of the crosslinked polyacrylamide may vary as long as the molecules that make up EGF and EGF-2 are capable of penetrating the pores of the gel. Advantageously, the polyacrylamide gel exclusion limits are about 5,000 to 50,000 daltons, preferably about 10,000 to 30,000 daltons. A particularly preferred crosslinked polyacrylamide gel is Bio-Gel P-10™, a product of Bio-Rad Laboratories, which has an exclusion limit of 20,000 daltons.

The starting materials for the process of the invention must be the submaxillary glands of adult male mice. No EGF or EGF-2 has been found in the submaxillary glands of female mice or immature male mice. Homogenization of the glands may be effected by any convenient means as by the use of a suitable blender. Likewise, separation of the crude homogenate into a solid fraction and a supernatant fraction may be effected by any suitable separation means such as by centrifugation.

In order to achieve the desired adsorption of epidermal growth factors on the polyacrylamide gel the separated supernatant fraction is subjected to column chromatography on the crosslinked polyacrylamide gel at a low pH of about 1 to 3, preferably at a pH of about 1.5. Conducting the chromatography at a pH outside this range is unsatisfactory. Accordingly, the supernatant fraction is cleared of debris as by centrifugation and adjusted to the low acid pH before passage through the polyacrylamide gel column.

The polyacrylamide column is eluted with any suitable elutant, preferably a HCl-NaCl buffer and the progress of the elution is followed in fractions eluate by optical density determinations at 280 mu and immunoassays. Most of the protein in the homogenate elutes prior to the column volume. After the passage of one column volume of elutant there is but a trace of epidermal growth factors. Most of the biologically active material appears after about 1.5 column volumes in a small ultraviolet absorbing peak. This material when collected and neutralized is found to be about 98–99% pure.

In accordance with the preferred embodiment of the invention the epidermal growth factors thus obtained from the polyacrylamide chromography are subjected to diethylaminoethyl-cellulose ion exchange chromotography at a pH of above about 4, preferably a pH of about 5 to 7 which results in adsorption of essentially all the ultraviolet light absorbing biologically active material. Elution of the adsorbed biologically active material from the diethylaminoethyl cellulose column is achieved in the conventional manner employing an increasing salt gradient at a pH of about 4, preferably a pH of about 5 to 7. A particularly preferred salt for establishing the increasing gradient is ammonium acetate. The biologically active material is pooled, neutralized and preferably lyophilized to provide epidermal growth factors of very high purity.

Figure 2:
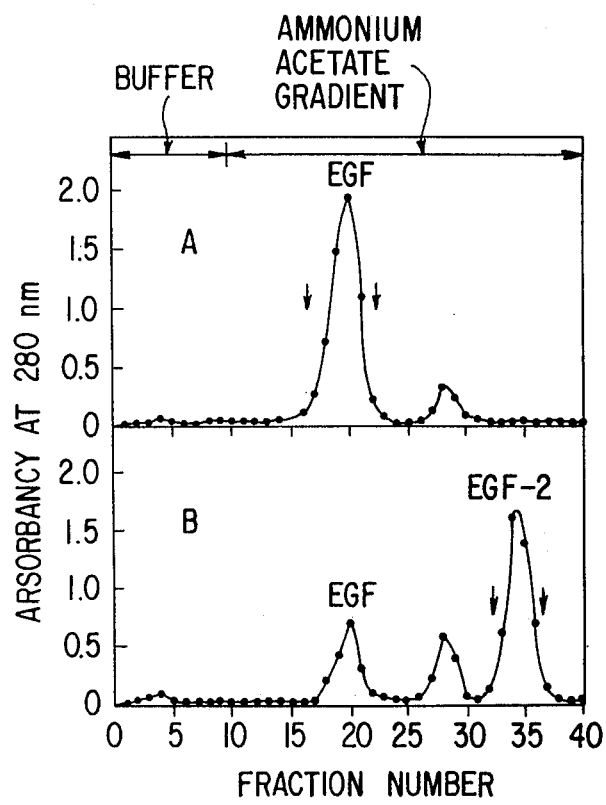

The present invention will be further illustrated by the following examples. In the examples reference will be made to the attached drawing in which FIG. 1 represents chromatography of crude submaxillary gland extract on Biogel P-10 and FIG. 2 represents DEAE-cellulose chromatography of EGF (A) and EGF-2 (B) obtained from the Biogel P-10 column.

EXAMPLE I

150 Adult male Swiss Webster mice weighing in excess of 40 g were killed with chloroform and the submaxillary glands were excised and stored frozen on Dry Ice. The frozen glands (29.4 g) were thawed and homogenized with 118 ml of cold 0.05 M acetic acid in a Waring Blendor at 4° for 3 min (final pH 4.5). The resulting crude homogenate was then frozen in a Dry Ice-alcohol bath. After thawing, the material was centrifuged at 100,000 × g for 30 min. The resulting supernatant was collected by decantation through glass wool to remove floating fat. The pellet was washed with 74 ml of $5 \times 10^{-4}$ M acetic acid followed by centrifugation as above. The wash was repeated once, and the supernatant fractions were combined and lyophilized. The pellet was discarded.

The dry residue was suspended in approximately 7 ml of cold 1 N HCl in order to rapidly lower the pH. The mixture was then diluted with 18 ml of 0.05 N HCl. The pH was adjusted to 1.5 and the mixture was centrifuged at 100,000 × g for 30 min at 4°. The pellet was washed once with 3 ml of 0.05 N HCl, recentrifuged, and the supernatants were combined to yield approximately 23 ml of clear rust colored solution. The clear rust colored solution was chromatographed on a Bio-Gel P-10 column at 5°. The Bio-Gel P-10 (100 to 200 mesh) column was a reverse flow column (5 × 90 cm) prepared and equilibrated with HCl-NaCl buffer (0.05 N HCl containing 0.15 M NaCl) at 5°. The column was packed at 40 cm head pressure and operated at 36 cm head pressure with a flow rate of 45 to 50 ml per hour. Column eluates were monitored both by the ISCO flow monitor at 280 nm and manually using a Beckman DU spectrophotometer at 280 nm. A typical elution pattern is shown in FIG. 1. As expected, most of the protein in the homogenate was eluted prior to the column volumn; however, no anti-EGF immunoreactive material was detectable. Although a trace of immunoreactive material was detected just after the passage of one column volume of buffer (see FIG. 1), most of the immunoreactive material was adsorbed to the column and appeared in a small ultraviolet absorbing peak which eluted after about 1.6 column volumes. The material between the arrows (FIG. 1) was pooled, neutralized to pH 5 to 7 with 1 N NaOH and concentrated to about 10 ml by pressure ultrafiltration (UM 2 membrane). Then, 250 ml of 0.02 M ammonium acetate, pH 5.6, was added and the solution was reconcentrated to about 10 ml. This preparation contained, on the average, a total of 55 to 65 absorbance units at 280 nm. The preparation (10 to 15 ml) was applied to a DEAE-cellulose column. The column (1.5 × 20 cm) of DEAE-cellulose was prepared and equilibrated with 0.02 M ammonium acetate, pH 5.6 at 5°. The flow rate was maintained at 12 ml per hour using a Buchler polystaltic pump. Protein adsorbed to the DEAE-cellulose was eluted with a 0.02 M to 0.2 M ammonium acetate gradient formed by allowing 0.2 M ammonium acetate buffer (pH 5.60) to flow into a 125-ml constant volume mixing chamber containing the 0.02 M buffer, pH 5.60. A typical elution profile is shown in FIG. 2A. Only one major and one minor symmetrical ultraviolet absorbing peak was obtained. The material in the major peak was pooled and lyophilized. It was then dissolved in 10 ml of 0.05 M acetic acid, relyophilized, and stored diseccated at 5°.

The resulting material is indistinguishable from the EGF previously isolated by the prior art methods referred to above on the basis of amino acid composition, $NH_2$- and COOH-terminal residues, polyacrylamide gel electrophoresis, Bio-Gel P-10 and DEAE-cellulose chromatography, immunodiffusion in agarose gels and biological activity. A comparison of the amino acid composition of EGF from the prior art method and EGF from the new method as well as EGF-2 is shown in the following Table I.

TABLE I

| Amino acid composition of EGF and EGF-2 | | |
|---|---|---|
| EGF | | |
| Amino acid | Old method[a] | New Method | EGF-2 |
| residues/mole[a] | | | |

TABLE I-continued

Amino acid composition of EGF and EGF-2

| Amino acid | EGF Old method[d] | EGF New Method | EGF-2 |
|---|---|---|---|
| Lysine | 0 (0) | 0 (0) | 0 (0) |
| Histidine | 0.92 (1) | 0.91 (1) | 0.97 (1) |
| Arginine | 3.92 (4) | 3.99 (4) | 2.98 (3) |
| Aspartic acid | 6.64 (7) | 6.74 (7) | 6.77 (7) |
| Threonine | 1.80 (2) | 1.78 (2) | 1.81 (2) |
| Serine | 5.32 (6) | 5.26 (6) | 5.24 (6) |
| Glutamic acid | 3.00 (3) | 3.00 (3) | 3.00 (3) |
| Proline | 2.10 (2) | 2.02 (2) | 1.88 (2) |
| Glycine | 5.94 (6) | 5.86 (6) | 5.82 (6) |
| Alanine | 0 (0) | 0 (0) | 0 (0) |
| Half-cystine | 4.23 (6)[b] | 4.20 (6) | 4.55 (6) |
| Valine | 1.51 (2) | 1.52 (2) | 1.40 (2) |
| Methionine | 0.94 (1) | 0.94 (1) | 1.21 (1) |
| Isoleucine | 1.45 (2) | 1.79 (2) | 1.59 (2) |
| Leucine | 3.93 (4) | 4.17 (4) | 3.09 (3) |
| Tyrosine | 4.89 (5) | 4.93 (5) | 4.92 (5) |
| Phenylalanine | 0 (0) | 0 (0) | 0 (0) |
| Tryptophan[c] | 2.18 (2) | 2.20 (2) | 2.19 (2) |

[a]Calculated on the basis of 3.00 glutamic acid residues per mole. The samples were hydrolyzed with 6 N HCl at 110° for 24 hours.
[b]Assumption based on data presented in SAVAGE, C. R., JR., INAGAMI, T. and COHEN, S. (1972) J. Biol. Chem. 247, 7612–7621.
[c]Determined by the spectrophotometric method of GOODWIN, T. W., and MORTON, R. A. (1946) Biochem. J. 40, 628–632.
[d]COHEN, S. (1962) J. Biol. Chem., 237, 1555–1562.

The material in the minor peak (FIG. 2A) was also biologically active and precipitated with the EGF antibody. The difference between these two forms is not known. The amino acid compositions of the proteins in the two peaks, however, is very similar, but due to the small amounts of materials available in the small peak, it was not further investigated.

The method of the present invention offers not only a marked reduction in time and number of steps required, but also provides a greatly improved yield. For example, the two-step procedure can be completed in less than a week. A comparison of the yields of EGF obtained by the process of the invention with that originally described in Cohen, S. (1962) J. Biol. Chem. 237, 1555–1562, in which an estimated 20% recovery of EGF was obtained, is shown in Table II.

TABLE II

Comparison of yields of EGF using new and old procedures

| Method of isolation | Mice | Wet weight of salivary glands | Total EGF recovered | Average yield of EGF |
|---|---|---|---|---|
| | number | g | mg | mg/g wet weight |
| Old | 150 | 21–23 | 4–6 | 0.23 |
| New | 150 | 29–31 | 16–21 | 0.62 |

It can be seen from the table that the process of the invention improved the average recovery of EGF per g of tissue by almost 3-fold; the use of larger mice further improved the yield of EGF per animal approximately 4-fold.

EXAMPLE II

To prepare EGF-2, a procedure similar to that described in Example I above was followed except that the submaxillary glands were homogenized in 1.0 M acetic acid instead of 0.05 M acetic acid to yield an extract with a final pH of 3.2 to 3.5, and the pellets obtained after centrifugation were washed with 0.05 M acetic acid.

The subsequent procedures for the isolation of EGF-2 were identical to those described for the preparation of EGF in Example I. Upon gel filtration on the acid Bio-Gel P-10 column, EGF-2 was slightly more retarded than EGF and appeared between 3200 and 3600 ml (see FIG. 1). All of the immunoreactive fractions (between 2800 and 3600 ml) were pooled and chromatographed on DEAE-cellulose in a manner identical with that described for EGF in Example I. The resulting elution pattern, shown in FIG. 2B, indicated that EGF-2 and EGF were readily resolved.

As can be seen from Table I, identical analyses were obtained for the two EGF preparations, whereas EGF-2 contained only 3 arginine and 3 leucine residues instead of 4 residues of each.

Extensive digestion of either preparation of EGF with carboxypepidase B resulted in the liberation of 1 mole of arginine and 1 mole of leucine per mole of peptide. Digestion of EGF-2 with carboxypeptidase B did not result in the liberation of any amino acid.

Digestion of EGF-2 with carboxypeptidase A resulted in the liberation of glutamic acid and tryptophan. In contrast, EGF was inert to digestion with carboxypeptidase A. It was also found that the sequence of the COOH-terminal region of EGF is -Trp-Trp-Glu-Leu-Arg-COOH. This finding supports the interpretation that EGF-2 is derived from EGF by the removal of the COOH-terminal two amino acid residues.

As expected, EGF and EGF-2 are clearly separable by electrophoresis at pH 9.5 on polyacrylamide gels. Treatment of EGF with carboxypeptidase B, to remove the COOH-terminal Leu-Arg residues, results in a product which coelectrophoreses with EGF-2.

EXAMPLE III

The biological activity of EGF and EGF-2 was compared by giving newborn mice daily injections in the amounts indicated in Table III below. According to procedures described in Cohen, S. (1962) J. Biol. Chem. 237, 1555–1562, controls received injections of distilled water. At least two mice were used for each determination. The results of the comparison are shown in the following Table III.

TABLE III

Comparison of the biological activity of EGF and EGF-2

| Preparation | Dosage | Eyelids open |
|---|---|---|
| | μg/g body wt/day | day |
| EGF (old method) | 0.25 | 10 |
| | 1.0 | 8 |
| EGF (new method) | 0.25 | 10 |
| | 1.0 | 8 |
| EGF-2 | 0.25 | 10 |
| | 1.0 | 7 |
| Control | 0 | 12 |

The data shows that epidermal growth factor lacking the COOH-terminal Leu-Arg residues is indistinguishable in biological activity from EGF. It may be precipitated with the antibody EGF.

It is claimed:

1. A process for the preparation of substantially pure epidermal growth factors which comprises homogenizing submaxillary glands of adult male mice, separating the resulting homogenate into a solid fraction and a supernatant fraction, passing the supernatant fraction through a column of crosslinked polyacrylamide gel at a pH of 1 to 3 to selectively adsorb epidermal growth factor from said supernatant fraction, eluting the column to recover a fractional eluate having epidermal growth activity and absorption of ultraviolet light of wave length about 280 $\mu$.

2. The process of claim 1 wherein said pH is about 1.5.

3. The process of claim 2 wherein the elution is effected with a hydrogen chloride-sodium chloride buffer.

4. The process of claim 1 wherein the pH of the homogenate is maintained at between 3 and 4.

5. The process of claim 1 wherein the pH of the homogenate is above 4 during said separation and the supernatant fraction is adjusted to a pH of between about 1 and 3.

6. The process of claim 1 wherein the crosslinked polyacrylamide gel has an exclusion limit of about 10,000 to 30,000 daltons.

7. The process of claim 5 wherein the pH of the supernatant fraction is about 1.5.

8. The process of claim 7 wherein the crosslinked polyacrylamide gel has an exclusion limit of 20,000 daltons.

9. A process for the production of high yields of pure epidermal growth factors which comprises homogenizing submaxillary glands of adult male mice, separating the resulting homogenate into a solid fraction and a supernatant fraction, passing the supernatant fraction through a column of crosslinked polyacrylamide gel at a pH of about 1 to 3 to selectively adsorb epidermal growth factors from said supernatant fraction, eluting the column to recover a fractional eluate having epidermal growth activity and adsorption of ultraviolet light of wave length about 280 mu, passing said fractional eluate through a column of diethylaminoethylcellulose at a pH of above about 4 to adsorb said epidermal growth factors therefrom and eluting the diethylaminoethylcellulose column with an increasing salt gradient at a pH of above about 4 to recover fractional eluates of increased purity having epidermal growth activity and absorption of ultraviolet light of wave length about 280 $\mu$.

10. The process of claim 9 wherein the supernatant fraction is passed through the column of crosslinked polyacrylamide gel at a pH of about 1.5

11. The process of claim 10 wherein the pH of the homogenate is between about 1 and 3.

12. The process of claim 9 wherein the pH of the homogenate is between 3 and 4.

13. The process of claim 9 wherein the pH of the homogenate is above 4 during said separation and the supernatant fraction is adjusted to a pH between about 1 and 3.

14. The process of claim 9 wherein the crosslinked polyacrylamide gel has an exclusion limit of 10 to 30,000 daltons.

15. The process of claim 14 wherein the homogenate is maintained at a pH of 1 to 3 or above 4 and the crosslinked polyacrylamide gel has an exclusion limit of 20,000 daltons.

* * * * *